(12) United States Patent
Jiaang et al.

(10) Patent No.: US 11,299,489 B1
(45) Date of Patent: Apr. 12, 2022

(54) THIAZOLE COMPOUNDS AS PROTEIN KINASE INHIBITORS

(71) Applicants: NATIONAL HEALTH RESEARCH INSTITUTES, Miaoli County (TW); Taivex Therapeutics Corporation, Taipei (TW)

(72) Inventors: Weir-Torn Jiaang, Taipei (TW); Yu-Sheng Chao, New Taipei (TW)

(73) Assignees: National Health Research Institutes, Miaoli County (TW); Taivex Therapeutics Corporation, Taipei (TW)

(*) Notice: Subject to any disclaimer, the term of this patent is extended or adjusted under 35 U.S.C. 154(b) by 7 days.

(21) Appl. No.: 16/952,600

(22) Filed: Nov. 19, 2020

(51) Int. Cl.
*C07D 417/14* (2006.01)
*A61P 35/02* (2006.01)

(52) U.S. Cl.
CPC ............ *C07D 417/14* (2013.01); *A61P 35/02* (2018.01)

(58) Field of Classification Search
CPC ............................... C07D 417/14; A61P 35/02
USPC .................................................... 514/252.18
See application file for complete search history.

(56) References Cited

U.S. PATENT DOCUMENTS 10,300,061 B2   5/2019   Jiaang et al.

OTHER PUBLICATIONS

Christopher et al. Drug Metabolism and Disposition (2008), 36)7), 1357-1364.*

* cited by examiner

*Primary Examiner* — Kahsay Habte

(74) *Attorney, Agent, or Firm* — Muncy, Geissler, Olds & Lowe, P.C.

(57) ABSTRACT

Thiazole compounds of Formula (I) shown below and pharmaceutical compositions containing one of such compounds:

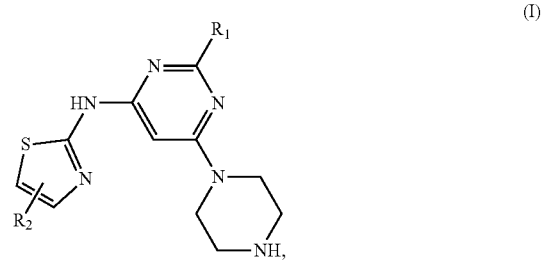

(I)

wherein $R_1$ and $R_2$ are defined in the specification. Also disclosed are methods of inhibiting a tyrosine kinase and treating cancer associated with a tyrosine kinase with one of the thiazole compounds.

20 Claims, 1 Drawing Sheet

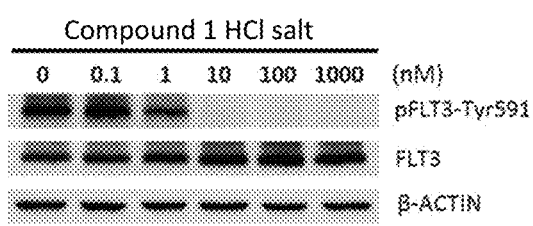
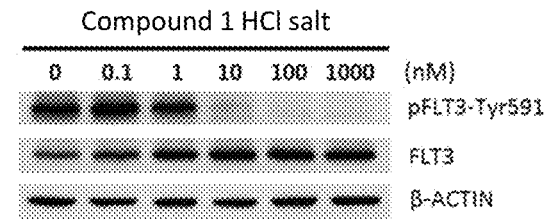
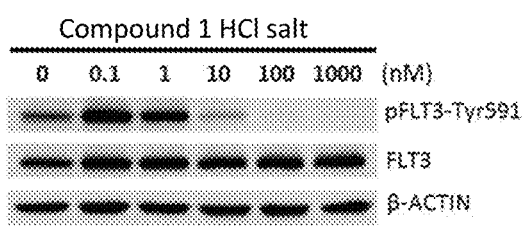
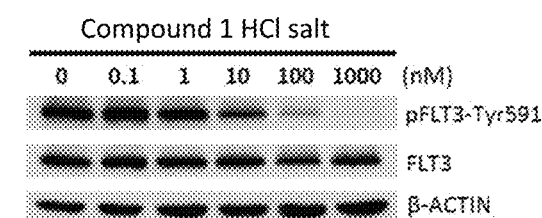
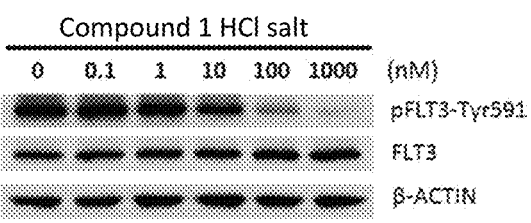

THIAZOLE COMPOUNDS AS PROTEIN KINASE INHIBITORS

BACKGROUND

Protein kinases are important in cellular signal pathways that regulate various cell functions, including differentiation, proliferation, migration, and apoptosis. Deregulation of protein kinases is implicated in cancer and a number of other diseases.

Tyrosine kinases, a subclass of protein kinases, regulate target protein function through transfer of phosphate from ATP to the hydroxyl group of a target protein tyrosine. FMS-like tyrosine kinase 3 ("FLT3"), and tyrosine-protein kinase Kit ("c-Kit") are tyrosine kinases that have been studied as attractive therapeutic targets in cancer treatment.

Mutations of FLT3, a receptor tyrosine kinase, can lead to development of cancer, e.g., acute myeloid leukemia. See Pratz et al., *Current Drug Targets*, 2010, 11(7), 781-9.

c-Kit, also a receptor tyrosine kinase, is involved in intracellular signaling. The mutated form of c-Kit plays a crucial role in occurrence of some cancers. Inhibition of c-Kit has proved to be effective in treating gastrointestinal stromal tumor, acute myeloid leukemia, and melanoma. See Babaei et al., *Drug Des Devel Ther.*, 2016 10, 2443-2459.

Thiazole compounds, extensively explored as potent tyrosine kinase inhibitors, present several challenges as drug candidates. They possess poor kinase selectivity, often cause animal death in toxicity studies, and generally lack adequate in vivo exposure to exert desirable efficacy in pre-clinical or clinical studies.

There is a need to develop new thiazole compounds that specifically inhibit certain tyrosine kinases, demonstrate desirable safety profiles, and exert sufficient in vivo efficacy in treating target cancers.

SUMMARY

The present invention is based on unexpected discoveries that certain thiazole compounds effectively inhibit multiple tyrosine kinases, e.g., FLT3, and c-Kit.

In one aspect, this invention relates to thiazole compounds of Formula (I):

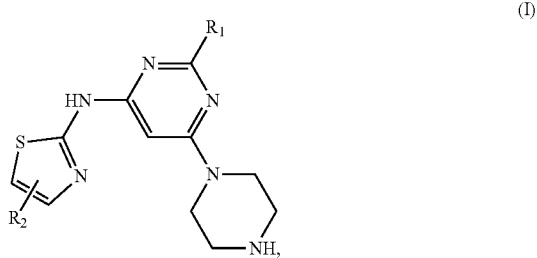

in which $R_1$ is $C_{1-6}$ alkyl; and $R_2$ is heteroaryl.

The term "alkyl" herein refers to a straight or branched hydrocarbon group, containing 1-6 carbon atoms (e.g., $C_1$-$C_4$, $C_1$-$C_3$ and $C_1$-$C_2$). Examples include methyl, ethyl, n-propyl, i-propyl, n-butyl, i-butyl, and t-butyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include thiophenyl, triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl.

Alkyl and heteroaryl mentioned herein include both substituted and unsubstituted moieties, unless specified otherwise. Possible substituents on heteroaryl include $C_{1-10}$ alkyl, $C_{2-10}$ alkenyl, $C_{2-10}$ alkynyl, $C_{3-20}$ cycloalkyl, $C_{3-20}$ cycloalkenyl, $C_{1-20}$ heterocycloalkyl, $C_{1-20}$ heterocycloalkenyl, alkoxy, aryl, aryloxy, heteroaryl, heteroaryloxy, amino, $C_{1-10}$ alkylamino, $C_{1-20}$ dialkylamino, arylamino, diarylamino, hydroxyl, halogen, thio, $C_{1-10}$ alkylthio, arylthio, $C_{1-10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl include all of the above-recited substituents except $C_{1-10}$ alkyl, $C_{2-10}$ alkenyl, and $C_{2-10}$ alkynyl. Cycloalkyl, heterocycloalkyl, aryl, and heteroaryl can also be fused with each other.

The thiazole compounds described above include the compounds themselves, as well as their salts, prodrugs, and solvates, if applicable. A salt, for example, can be formed between an anion and a positively charged group (e.g., amino) on a thiazole compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a thiazole compound. Suitable cations include sodium ion, potassium ion, magnesium ion, calcium ion, and an ammonium cation such as tetramethylammonium ion. The thiazole compounds also include those salts containing quaternary nitrogen atoms. Examples of prodrugs include esters and other pharmaceutically acceptable derivatives, which, upon administering to a subject, are capable of providing active thiazole compounds. A solvate refers to a complex formed between an active thiazole compound and a pharmaceutically acceptable solvent. Examples of a pharmaceutically acceptable solvent include water, ethanol, isopropanol, ethyl acetate, acetic acid, and ethanolamine.

In another aspect, this invention relates to a method for inhibiting a tyrosine kinase, e.g., FLT3, and c-Kit. The method includes contacting the tyrosine kinase with an effective amount of one or more of the above-described thiazole compounds.

Also within the scope of this invention is a method for treating cancer associated with a tyrosine kinase. The method includes administering to a subject in need thereof an effective amount of one or more of the thiazole compounds of Formula (I) described above.

The tyrosine kinase associated to a cancer can be a wild type or mutant. Examples of the tyrosine kinase include, but are not limited to, FLT3, FLT4, VEGFR, platelet-derived growth factor receptor (PDGFR) A, PDGFR B, c-Kit, c-Src (SRC), tyrosine-protein kinase Lyn (LYN) A, LYN B, rearranged during transfection tyrosine kinase (RET), lymphocyte-specific protein tyrosine kinase, Gardner-Rasheed feline sarcoma viral oncogene homolog, discoidin domain receptor 1, kinase insert domain receptor, B lymphocyte kinase, tyrosine-protein kinase Yes, Abelson murine leukemia viral oncogene homolog 1 (ABL1), tyrosine-protein kinase Tek, RET V804L, RET Y791F, FLT3 D835Y, PDGFR A V561D, or ABL1 T315I.

In an exemplary method, the thiazole compounds of Formula (I) are used for treating cancer associated with FLT3, or c-Kit.

Examples of the cancer include acute myeloid leukemia, chloroma, chronic myelogenous leukemia, acute lymphoblastic leukemia, chronic lymphocytic leukemia, Hodgkin's disease, non-Hodgkin's lymphoma, B-cell lymphoma, multiple myeloma, Waldenstrom's macroglobulinemia, myelodysplastic syndrome, pancreatic cancer, bladder cancer, colorectal cancer, breast cancer, male genital tract cancer, renal cancer, hepatocellular cancer, lung cancer, ovarian cancer, cervical cancer, uterus cancer, gestational trophoblastic disease, gastric cancer, bile duct cancer, gallbladder cancer, small intestine cancer, esophageal cancer, oropharyngeal cancer, hypopharyngeal cancer, eye cancer, nerve cancer, head and neck cancer, melanoma, plasmacytoma, endocrine gland neoplasm, neuroendocrine cancer, brain tumor, bone cancer, and sarcoma (e.g., gastrointerstinal stromal tumor or GIST).

In an exemplary method, the thiazole compounds of Formula (I) are used for treating acute myeloid leukemia.

Further within the scope of this invention is a pharmaceutical composition containing one or more of the above-described thiazole compounds of Formula (I). The pharmaceutical composition can be used for treating cancer.

This invention also encompasses use of one or more of the above-described thiazole compounds of Formula (I) for the manufacture of a medicament for treating cancer.

The term "treating" or "treatment" refers to administering one or more of the thiazole compounds to a subject, who has an above-described disease, i.e., cancer, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it. "An effective amount" refers to the amount of an active compound that is required to confer the therapeutic effect. Effective doses will vary, as recognized by those skilled in the art, depending on the types of disease treated, route of administration, excipient usage, and the possibility of co-usage with other therapeutic treatment.

To practice the method of the present invention, a composition having one or more of the above-described thiazole compounds can be administered parenterally, orally, nasally, rectally, topically, or buccally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more of the above-described thiazole compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active 1,5-diphenyl-penta-1,4-dien-3-one compound. Examples of other carriers include colloidal silicon oxide, magnesium stearate, cellulose, sodium lauryl sulfate, and D&C Yellow #10.

The details of one or more embodiments of the invention are set forth in the description below. Other features, objects, and advantages of the invention will be apparent from the description and from the claims.

DETAILED DESCRIPTION

Disclosed in detail are thiazole compounds of Formula (I):

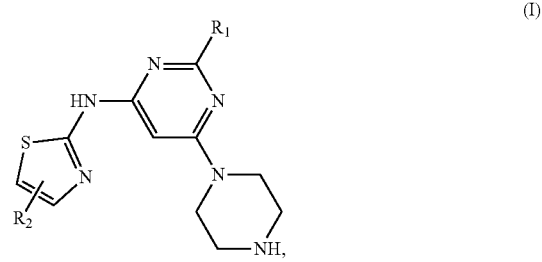

in which variables $R_1$ and $R_2$ are defined in the SUMMARY section above.

Typically, compounds of Formula (I) have $R_1$ being $C_{1-6}$ alkyl. One example of $R_1$ is methyl.

Typically, compounds of Formula (I) have $R_2$ being 5- or 6-membered heteroaryl. Exemplary compounds have $R_2$ being 6-membered heteroaryl. One example of $R_2$ is pyridyl.

A group of the above-described novel thiazole compounds are compounds of Formula (II):

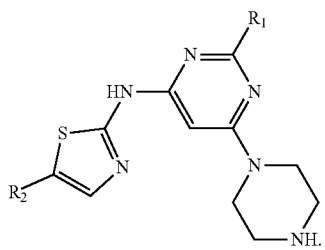

(II)

In one subset, compounds of Formula (II) have $R_1$ being methyl.

In another subset, compounds of Formula (II) have $R_2$ being 6-membered heteroaryl.

In further another subset, compounds of Formula (II) have $R_2$ being pyridyl.

Exemplary compounds include, but are not limited to,

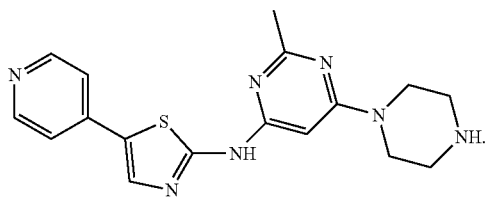 [SMILES: Cc1nc(Nc2ncc(-c3ccncc3)s2)cc(N2CCNCC2)n1]

Also within this invention is a pharmaceutical composition containing one or more of the thiazole compounds of Formula (I) for treating cancer.

Further covered by this invention is a method for treating cancer, the method including administering to a subject in need thereof an effective amount of a compound of Formula (I).

Synthetic chemistry transformations and protecting group methodologies (protection and de-protection) used for synthesizing the compounds of Formula (I) are well known in the art. See, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis ($2^{nd}$ ed., John Wiley and Sons 2009); and G. J. Yu et al., *J. Med. Chem.* 2008, 51, 6044-6054.

The compounds of Formula (I) thus prepared can be initially screened using biochemical assays, e.g., the kinase assays described in EXAMPLES 2-3 below, or cellular assays, e.g., the in vitro anticancer activity assay described in EXAMPLES 4-5 below, for their potency in inhibiting tyrosine kinases or inhibiting the growth of cancer cells expressing certain tyrosine kinases. They can be subsequently evaluated using in vivo assays, e.g., a xenograft animal model assay, for their activity in suppressing tumor growth in a mammal. The selected compounds can be further tested to verify their efficacy in treating cancer. For example, a compound can be administered to an animal (e.g., a mouse) having cancer and its therapeutic effect is then assessed, e.g. the animal study described in EXAMPLE 6. Based on the results, appropriate dosage ranges and administration routes can be investigated and determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference in their entirety.

BRIEF DESCRIPTION OF THE DRAWINGS

The sole FIGURE shows results of Western Blot Analysis in EXAMPLE 5.

EXAMPLE

Shown in EXAMPLE 1 below are the synthesis and characterization of an exemplary compound of Formula (I). The analytical data for the compound thus prepared are also set forth in EXAMPLE 1 and the procedures for testing the compound are described in EXAMPLES 2-6 that follow.

All chemicals and solvents were purchased from commercial suppliers and used as received. All reactions were carried out under an atmosphere of dry nitrogen. Reactions were monitored by TLC using Merck 60 F254 silica gel glass backed plates (5×10 cm); and zones were detected visually under ultraviolet irradiation (254 nm) or by spraying with phosphomolybdic acid reagent (Aldrich) followed by heating at 80° C. All flash column chromatography was performed with Merck Kieselgel 60, No. 9385, 230-400 mesh ASTM silica gel as the stationary phase. Proton ($^1$H) nuclear magnetic resonance spectra were measured on a Varian Mercury-300 or Varian Mercury-400 spectrometer. Chemical shifts were recorded in parts per million (ppm) on the delta ($\delta$) scale relative to the resonance of the solvent peak. The following abbreviations were used to describe coupling: s=singlet; d=doublet; t=triplet; q=quartet; quin=quintet; br=broad; and m=multiplet. LCMS data were measured on an Agilent MSD-1100 ESI-MS/MS, Agilent 1200 series LC/MSD VL, and Waters Acquity UPLC-ESI-MS/MS system.

Example 1: Synthesis of Compound 1

Compound 1 were prepared according to the synthetic route shown in Scheme 1 below. Among the listed reagents, DMSO is dimethyl sulfoxide and HCl is hydrochloric acid. Starting material A was prepared according to previously published protocols (J. Med. Chem. 2019, 62, 11135).

[Scheme 1]

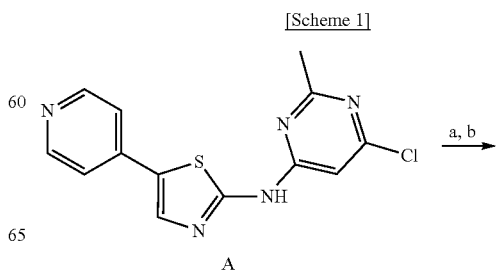

A

-continued

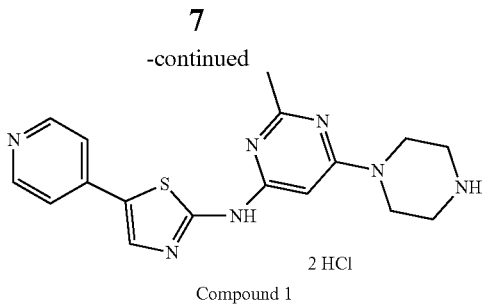

Compound 1 · 2 HCl

Reagents and conditions: (a) Piperazine, DMSO, 70° C.; and (b) 6N HCl, 0° C.

A mixture of compound A (2 mmol) and piperazine (20 mmol) in dimethyl sulfoxide (2 mL) was heated at 70° C. for 2 h. After cooling to room temperature, the mixture was diluted with water (50 mL). The precipitate was collected by filtration, washed with water (10 mL) and dried in vacuo. The residue was purified by chromatography on aluminium oxide (0.5% to 1.5% MeOH/CH$_2$Cl$_2$ gradient) to give free-base of compound 1 as an off-white solid.

To a stirred 6 N HCl (2 mL) at 0° C. was added the above solid and the solution was filtered through a 0.45 μm PVDF membrane. To the stirred filtrate was added acetone (20 mL) dropwise over the course of 1 h and was stirred for an additional 1 h at 0° C. The precipitate was collected by filtration, washed with acetone (10 mL) and dried in vacuo to give the HCl salt of compounds 1 as a yellow solid (85%).

2-Methyl-6-(piperazin-1-yl)-N-[5-(pyridine-4-yl)-1,3-thiazol-2-yl]pyrimidin-4-amine dihydrochloride (Compound 1). $^1$H NMR (400 MHz, D$_2$O): δ8.65 (d, 2H, J=7.2 Hz), 8.32 (s, 1H), 8.11 (d, J=7.2 Hz, 2H), 6.41 (s, 1H), 4.08 (t, J=5.4 Hz, 4H), 3.45 (t, J=5.2 Hz, 4H), 2.66 (s, 3H); $^{13}$C NMR (100 MHz, D$_2$O): δ 164.3, 161.4, 159.3, 148.5, 141.3, 140.8, 125.9, 121.8, 84.7, 42.5, 42.1, 21.8; MS (ES$^+$) m/z calcd. for C$_{17}$H$_{19}$N$_7$S: 353.1; found: 354.1 [M+H]$^+$.

Example 2: Inhibiting FLT3 Activity

A study was carried out as follows to test compound 1 HCl salt prepared according to EXAMPLE 1 in inhibiting FLT3 activity.

GST-FLT3-KD$^{WT}$ containing the FLT3 kinase catalytic domain (residues Y567-5993) was expressed in Sf9 insect cells transfected the baculovirus containing pBac-PAK8-GST-FLT3-KD plasmid. An FLT3$^{WT}$ Kinase-Glo assay was carried out in 96-well plates at 30° C. for 4 h to test compound in a final volume of 50 μL including the following components: 75 ng GST-FLT3-KD$^{WT}$ proteins, 25 mM HEPES, pH 7.4, 4 mM MnCl$_2$, 10 mM MgCl2, 2 mM DTT, 0.02% Triton X-100, 0.1 mg/mL bovine serum albumin, 25 μM Her2 peptide substrate, 0.5 mM Na$_3$VO$_4$, and 1 μM ATP. Following incubation, 50 μL Kinase-Glo Plus Reagent (Promega, Madison, Wis., USA) was added to each well and the mixture was incubated at 25° C. for 20 min. A 70-μL aliquot of each reaction mixture was transferred to a black microtiter plate and the luminescence was measured on Wallac Vector 1420 multilabel counter (PerkinElmer, Shelton, Conn., USA).

Compounds 1 showed IC$_{50}$ (the concentration of an inhibitor where the response is reduced by half) values lower than 100 nM.

Example 3: Inhibiting c-Kit Activity

A study was carried out as follows to test compound 1 HCl salt prepared according to EXAMPLE 1 in inhibiting c-Kit activity.

The N-terminal His-tagged human c-KIT (residues T544-V976) recombinant proteins, expressed in 519 baculovirus-insect cell expression systems, were purified for c-KIT ADP Kinase-Glo assay. A c-Kit-ADP Kinase-Glo assay was carried out in 96-well plates at 30° C. for 150 mins with a final volume of 10 μL, including 40 mM Tris pH 7.4, 20 mM MgCl2, 2 mM MnCl$_2$, 2 mM DTT, 0.01% BSA, 20 μM ATP, 20 μM poly(Glu,Tyr) 4:1 peptide, 0.1 mM Na$_3$VO$_4$, 250 ng of recombinant c-Kit proteins, and a tested compound at the indicated concentration. The reactions were stopped by the addition of 5 μL ADP-Glo™ Reagent (Promega, Madison, Wis., USA) at 25° C. with 40 min incubation, followed by 10 μL of kinase detection reagent for a further 30 min. Finally, a 30 μL aliquot of each reaction mixture was transferred to a black microtiter plate and the luminescence was measured on Wallac Vector 1420 multilabel counter (Perkin-Elmer, Shelton, Conn., USA).

Compounds 1 showed IC$_{50}$ values lower than 100 nM.

Cell Lines and Cell Culture

MV4:11, BaF3 and HEK293T cell lines were obtained from American Type Culture Collection (ATCC, Manassas, Va., USA). MOLM-13 cell line was purchased from the Deutsche Sammlung von Microorganismen and Zellkulturen GmbH (DSMZ, Braunschweig, Germany). The GIST-T1 cell line was obtained from COSMO BIO CO., LTD (Tokyo, Japan). The GIST-T1, MOLM-13, MV4:11, BaF3, BaF3/FLT3-D835Y, BaF3/FLT3-ITD-F691L and BaF3/FLT3-ITD-D835Y cells were maintained in RPMI 1640 medium supplemented with 10% fetal bovine serum (FBS), 10 U/mL penicillin, and 100 μg/mL streptomycin at 37° C. and 5% CO$_2$. The kasumin-1 cells were cultured in RPMI 1640 medium supplemented with 20% fetal bovine serum (FBS), 1 mM Hepes, 1 mM sodium pyruvate, 10 U/ml penicillin, and 100 μg/ml streptomycin. The HEK293T and FLT3-transfected HEK293T cells were cultured in DMEM (Invitrogen, USA) medium with 10% FBS fetal bovine serum.

GIST882, GIST48 and GIST430 cells were all cultured in incubators maintained at 37° C. and 5% CO$_2$. GIST882 was cultured in RPMI-1640 supplemented with 20% fetal bovine serum (FBS). GIST48 was cultured with F10 supplemented with 20% FBS, 0.5% Mito, serum extender (BD Bioscience, 355006) and 1% pituitary extract bovine (BD Bioscience 354123). GIST430 was cultured in IMDM supplemented with 20% FBS. GIST882, GIST430 and GIST48 cells were provided by Dr. Jonathan A. Fletcher (Harvard Medical School, US).

In Vitro Anticancer Activity

Example 4: MTS Cell Viability Assay

A study was carried out as follows to evaluate in vitro anticancer activity of test compound 1 HCl salt prepared according to EXAMPLE 1 using cell lines and MTS cell viability assays (MTS represents 3-(4,5-dimethylthiazol-2-yl)-5-(3-carboxymethoxyphenyl)-2-(4-sulfophenyl)-2H-tetrazolium).

Cell viability assay was performed by seeding 1×10$^4$ cells (MOLM-13, MV4:11, BaF3, BaF3/FLT3-D835Y, BaF3/FLT3-ITD-D835Y and BaF3/FLT3-ITD-F691L) per well in a 96-well culture plate. GIST-T1 cells were seeded in 96-well culture plate at density of 8×10$^3$ cells/100 μL. After 16 h, cells were then treated with vehicle or various concentrations of compound in medium for 72 h. The viable cells were quantitated using the CellTiter 96 AQueous MTS method (Promega, Madison, Wis., USA) according to the manufacturer's recommended protocol. The results were determined by measuring the absorbance at 490 nm using a plate reader (Victor2; PerkinElmer, Shelton, Conn., USA). The $IC_{50}$ value was defined as the amount of compound that caused 50% reduction in cell viability in comparison with DMSO-treated (vehicle) control and was calculated using Prism version 6 software (GraphPad, San Diego, Calif., USA).

GIST cells ($4 \times 10^4$) were treated with different dosage of compounds. The treated GIST882 cells were incubated for 144 h and GIST48 and GIST430 cells were incubated for 120 h at 37° C. in 5% $CO_2$. Cell proliferation was determined by incubating the cells with methylene blue (Clontech, CA, US) for 1 hour. The absorbance was measured at 450 nm using SpectraMax M5 microplate reader (Molecular Devices, US).

The $GI_{50}$ (the concentration for 50% of maximal inhibition of cell proliferation) values of test compound 1 HCl salt of Formula (I) are shown in the table 1 below.

TABLE 1

| | $GI_{50}$ (nM) | | | | | |
|---|---|---|---|---|---|---|
| | MOLM-13 | MV4:11 | GIST-T1 | GIST430 | GIST48 | GIST882 |
| Compound 1 HCl salt | 2.9 | 1.3 | 2.3 | 33 | 20 | 8.0 |
| | FLT3-ITD-F691L | FLT3-ITD-D835Y | FLT3-D835Y | | BaF3 + IL3* | |
| Compound 1 HCl salt | 95 | 53 | 14 | | 2,583 | |

*BaF3, a murine interleukin-3 (IL3) dependent pro-B cell line.

Example 5: Western Blot Analysis

Transfected HEK293T cells were lysed in lysis buffer (50 mM Tris, pH 8.0, 150 mM NaCl, 1% Triton X-100, 0.5% sodium deoxycholate, 0.1% SDS, 1 mM sodium orthovanadate, 1 mM PMSF, and 1 mM DTT). Protein lysates were resolved by SDS-PAGE and transferred onto a polyvinylidene difluoride (PVDF) membrane (Millipore, Bedford, Mass., USA). The membranes were immunoblotted with appropriate antibodies and detected using the SuperSignal reagent (Pierce, Rockford, Ill., USA) followed by exposure to X-ray film. The anti-pFLT3-Tyr591 (#3461, Cell Signaling Technology) antibody was purchased for Western blotting analysis.

As shown in the sole FIGURE, HEK293T cells expressing FLT3 (FLT3-WT (wild type), FLT3-ITD, FLT3-D835Y, FLT3-ITD-D835Y and FLT3-ITD-F691L) were analyzed. FLT3-transfected HEK293T cells were treated with compound 1 HCl salt at various concentrations for 1 h.

Example 6: Animal Study

Compound 1 HCl salt was formulated in 20% (2-hydroxypropyl)-β-cyclodextrin (Sigma). Kasumi-1 cells ($1 \times 10^6$/mouse) were injected subcutaneously into SCID (6 to 8 weeks old) male mice. Animals were randomized when average tumor volume reached approximately 230 mm$^3$ (n=8), followed by oral dosing of compound 1 HCl salt at the indicated dose levels and schedules shown in table below. Tumor size was measured with a digital caliper, and the tumor volume in mm$^3$ was calculated by the formula: Volume=(length×width$^2$)/2. All mice were monitored daily for signs of toxicity. Body weight and tumor size were measured twice times a week. Daily observations of health changes are possible during experimental time. At the end of the studies, animals will then be euthanized by carbon dioxide inhalation followed by cervical dislocation.

The results of the in vivo efficacy study on Kasumi-1 xenografts are shown in the table 2 below.

Table 2

| Dose | Treatment Schedule | Mortality (n = 6) | Body Weight Loss | Day 18 Tumor Size (mm$^3$) |
|---|---|---|---|---|
| Control | days 1-5 and 8-12 | 0/6 | No | 880 |
| Compound 1, 10 mg/kg | | 0/6 | No | 700 |
| Compound 1, 50 mg/kg | | 0/6 | No | 80 |

The results shown in the above examples indicate that the compound 1 or the salt thereof indeed has potency in inhibiting tyrosine kinases or inhibiting the growth of cancer cells expressing certain tyrosine kinases. Thus, the compound 1 or the salt thereof is capable of using for treating cancer associated with FLT3, or c-Kit.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I) below or a pharmaceutically acceptable salt thereof:

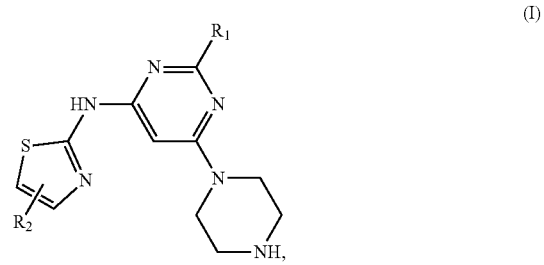

wherein,
R₁ is $C_{1-6}$ alkyl; and
R₂ is heteroaryl.

2. The compound or salt of claim 1, wherein R₁ is methyl.

3. The compound or salt of claim 1, wherein R₂ is 6-membered heteroaryl.

4. The compound or salt of claim 3, wherein R₂ is pyridyl.

5. The compound or salt of claim 1, wherein the compound is of formula (II):

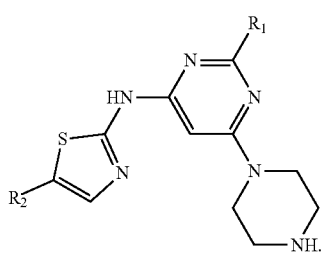

(II)

6. The compound or salt of claim 5, wherein R₁ is methyl.

7. The compound or salt of claim 5, wherein R₂ is 6-membered heteroaryl.

8. The compound or salt of claim 7, wherein R₂ is pyridyl.

9. The compound or salt of claim 1, which is

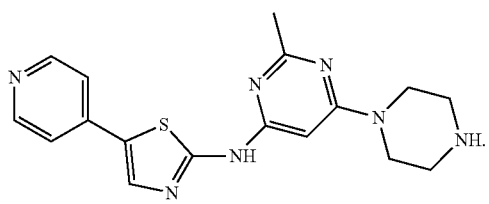

10. A pharmaceutical composition, comprising:
a pharmaceutically acceptable carrier; and
a compound of formula (I) below or a pharmaceutically acceptable salt thereof:

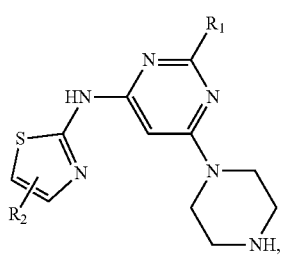

(I)

wherein,
R₁ is $C_{1-6}$ alkyl; and
R₂ is heteroaryl.

11. The pharmaceutical composition of claim 10, wherein the compound is

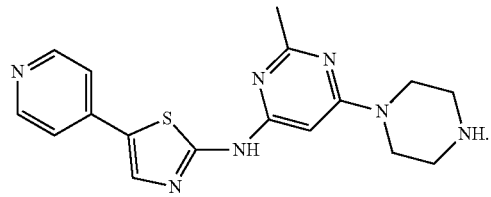 [SMILES: Cc1nc(Nc2ncc(-c3ccncc3)s2)cc(N2CCNCC2)n1]

12. A method of inhibiting a tyrosine kinase, comprising contacting the tyrosine kinase with an effective amount of a compound of formula (I) below or a pharmaceutically acceptable salt thereof:

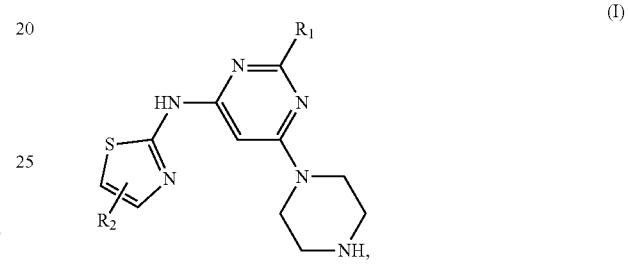

(I)

wherein,
R₁ is $C_{1-6}$ alkyl; and
R₂ is heteroaryl.

13. The method of claim 12, wherein the compound is

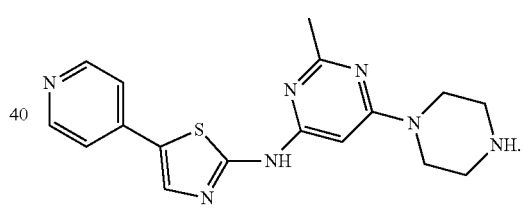

14. A method of treating cancer associated with a tyrosine kinase, the method comprising administering to a subject in need thereof an effective amount of a compound of formula (I) below or a pharmaceutically acceptable salt thereof:

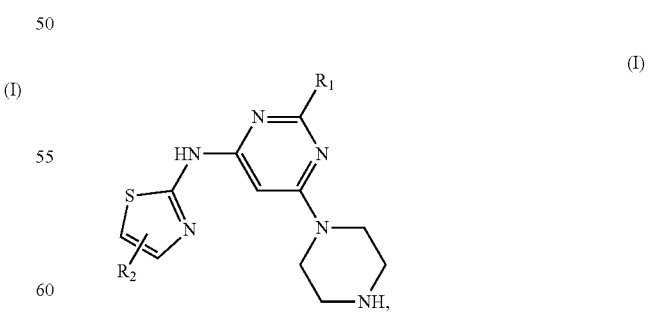

(I)

wherein,
R₁ is $C_{1-6}$ alkyl; and
R₂ is heteroaryl.

15. The method of claim 14, wherein the tyrosine kinase is FMS-like tyrosine kinase 3 (FLT3), FMS-like tyrosine kinase 4, vascular endothelial growth factor receptor (VEGFR), colony stimulating factor 1 receptor (CSF1R), platelet-derived growth factor receptor (PDGFR) A, PDGFR B, tyrosine-protein kinase Kit (c-KIT), c-Src (SRC), tyrosine-protein kinase Lyn (LYN) A, LYN B, rearranged during transfection tyrosine kinase (RET), lymphocyte-specific protein tyrosine kinase, Gardner-Rasheed feline sarcoma viral oncogene homolog, discoidin domain receptor 1, kinase insert domain receptor, B lymphocyte kinase, tyrosine-protein kinase Yes, Abelson murine leukemia viral oncogene homolog 1 (ABL1), tyrosine receptor kinase TRKA, TRKB, TRKC, ZAK/MLTK, IRAK4, RET V804L, RET Y791F, FLT3 D835Y, PDGFR A V561D, or ABL1 T315I.

16. The method of claim 15, wherein the tyrosine kinase is FLT3 or c-KIT.

17. The method of claim 16, wherein the cancer is acute myeloid leukemia, chloroma, chronic myelogenous leukemia, acute lymphoblastic leukemia, chronic lymphocytic leukemia, Hodgkin's disease, non-Hodgkin's lymphoma, B-cell lymphoma, multiple myeloma, Waldenstrom's macroglobulinemia, myelodysplastic syndrome, pancreatic cancer, bladder cancer, colorectal cancer, breast cancer, male genital tract cancer, renal cancer, hepatocellular cancer, lung cancer, ovarian cancer, cervical cancer, uterus cancer, gestational trophoblastic disease, gastric cancer, bile duct cancer, gallbladder cancer, small intestine cancer, esophageal cancer, oropharyngeal cancer, hypopharyngeal cancer, eye cancer, nerve cancer, head and neck cancer, melanoma, plasmacytoma, endocrine gland neoplasm, neuroendocrine cancer, brain tumor, bone cancer, or sarcoma.

18. The method of claim 17, wherein the cancer is acute myeloid leukemia.

19. The method of claim 14, wherein the compound is

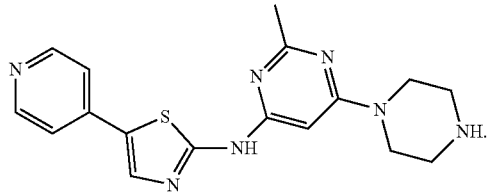 [SMILES: Cc1nc(Nc2ncc(-c3ccncc3)s2)cc(N2CCNCC2)n1]

20. The method of claim 18, wherein the compound is

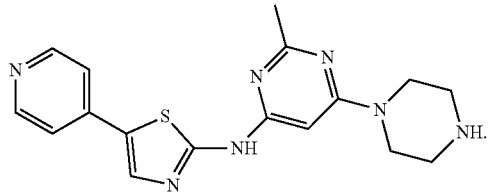 [SMILES: Cc1nc(Nc2ncc(-c3ccncc3)s2)cc(N2CCNCC2)n1]

* * * * *